US007919243B2

(12) United States Patent
Mach et al.

(10) Patent No.: US 7,919,243 B2
(45) Date of Patent: Apr. 5, 2011

(54) **METHOD FOR THE DETECTION OF *FUSARIUM GRAMINEARUM***

(75) Inventors: Robert Mach, Vienna (AT); Andreas Farnleitner, Wimpassing (AT); Georg Reischer, Vienna (AT)

(73) Assignee: Technische Universitat Wien, Vienna (AT)

( * ) Notice: Subject to any disclaimer, the term of this patent is extended or adjusted under 35 U.S.C. 154(b) by 725 days.

(21) Appl. No.: 11/570,226

(22) PCT Filed: Jul. 14, 2005

(86) PCT No.: PCT/EP2005/053394
§ 371 (c)(1),
(2), (4) Date: Dec. 7, 2006

(87) PCT Pub. No.: WO2006/005770
PCT Pub. Date: Jan. 19, 2006

(65) Prior Publication Data
US 2008/0008998 A1 Jan. 10, 2008

(30) Foreign Application Priority Data
Jul. 15, 2004 (AT) ................................ A 1209/2004

(51) Int. Cl.
*C12Q 1/68* (2006.01)
*C12P 19/34* (2006.01)
*C07H 21/04* (2006.01)

(52) U.S. Cl. ........................... 435/6; 435/91.2; 536/24.3

(58) Field of Classification Search ........................ None
See application file for complete search history.

(56) References Cited

FOREIGN PATENT DOCUMENTS

| | | |
|---|---|---|
| DE | 19615934 | 10/1997 |
| WO | WO 99/07884 | 2/1999 |
| WO | WO 03/027635 | 4/2003 |
| WO | WO 2004/029216 | 4/2004 |

OTHER PUBLICATIONS

Geiser et al., *FUSARIUM*-ID v. 1.0: A DNA sequence database for identifying *Fusarium*, European Journal of Plant Pathology 110: 473-479, Jun. 2004.*
Doohan et al., Development and Use of a Reverse Transcription-PCR Assay to Study Expression of Tri5 by *Fusarium* Species In Vitro and In Planta, Applied and Environmental Microbiology, Sep. 1999, p. 3850-3854 vol. 65, No. 9.*
Glass et al., Development of Primer Sets Designed for Use with the PCR to Amplify Conserved Genes from Filamentous Ascomycetes, Applied and Environmental Microbiology, Apr. 1995, p. 1323-1330 vol. 61, No. 4.*
Edwards et al., Review, PCR-based detection and quanti®cation of mycotoxigenic, fungi, Mycol. Res. 106 (9) : pp. 1005-1025 (Sep. 2002).*
Tan et al., Molecular Beacons: A Novel DNA Probe for Nucleic Acid and Protein Studies, Chem. Eur. J. 2000, 6, No. 7, pp. 1107-1111.*
Applied Biosystems, Designing TaqMan® MGB Probe and Primer Sets for Allelic Discrimination Assays Using Primer Express® Software Version 2.0, © 2002, pp. 1-15.*
Buck et al., Research Report, Design Strategies and Performance of Custom DNA Sequencing Primers, BioTechniques 27:528-536 (Sep. 1999), pp. 528-536.*
STRATAGENE, Catalog, 1988, p. 39.*
Atkins and Clark, "Fungal molecular diagnostics: a mini review," *J. Appl. Genet.*, 45:3-15, 2004.
Buerstmayr et al., "Molecular mapping of QTLs for *Fusarium* head blight resistance in spring wheat. I. Resistance to fungal spread (Type II resistance)," *Theor. Appl. Genet.*, 104:84-91, 2002.
Buerstmayr et al., "Molecular mapping of QTLs for *Fusarium* head blight resistance in spring wheat. II. Resistance to fungal penetration and spread," *Theor. Appl. Genet.*, 107:503-508, 2003.
Edwards et al., "Quantification of trichothecene-producing *Fusarium* species in harvested grain by competitive PCR to determine efficacies of fungicides against *Fusarium* head blight of winter wheat," *Appl. Environ. Microbiol.*, 67:1575-1580, 2001.
Fraaije et al., "Rapid detection and diagnosis of Septoria tritici epidemics in wheat using a polymerase chain reaction/PicoGreen assay," *J. Appl. Microbiol.*, 86:701-708, 1999.
Hue et al., "Specific detection of *Fusarium* species in blood and tissues by a PCR technique," *J. Clin. Microbiol.*, 37:2434-2438, 1999.
Jaeger et al., "Rapid detection and identification of Candida, *Aspergillus*, and *Fusarium* species in ocular samples using nested PCR," *J. Clin. Microbiol.*, 38:2902-2908, 2000.
Knoll et al., "Identification of *Fusarium graminearum* in cereal samples by DNA Detection Test Strips," *Lett. Appl. Microbiol.*, 34:144-148, 2002 (Abstract Only).
McCartney et al., "Molecular diagnostics for fungal plant pathogens," *Pest. Manag. Sci.*, 59:129-142, 2003.

(Continued)

*Primary Examiner* — Mark Staples
(74) *Attorney, Agent, or Firm* — Fulbright & Jaworski LLP

(57) ABSTRACT

A method for the detection of *Fusarium graminearum* (*Gibberella zeae*) comprising the steps: providing a sample containing a nucleic acid, contacting said sample with at least one forward primer and at least one reverse primer, wherein the at least one reverse primer hybridises within the β-tubulin nucleic acid sequence of *Fusarium graminearum* (*Gibberella zeae*) and comprises the nucleic acid sequence 5'-$R_1$TTTTCGT$X_1$GX2AGT-3' (SEQ ID NO 1), wherein $R_1$ comprises at least one nucleic acid residue of the β-tubulin nucleic acid sequence located upstream of the hybridisation site of the nucleic acid sequence SEQ ID NO 1 and subsequent to the nucleic acid sequence SEQ ID NO 1, $X_1$ is guanine, adenine or inosine, $X_2$ is cytosine, adenine or inosine, and wherein the at least one forward primer hybridises upstream of the hybridisation site of a nucleic acid sequence complementary to the at least one reverse primer, subjecting the sample contacted with the at least one forward primer and the at least one reverse primer to a nucleic acid amplification technique, and optionally determining the presence of *Fusarium graminearum* (*Gibberella zeae*) in a sample by detecting a nucleic acid amplification product.

32 Claims, 2 Drawing Sheets

OTHER PUBLICATIONS

O'Donnell and Cigelnik, "Two Divergent Intragenomic rDNA ITS2 Types within a Monophyletic Lineage of the Fungus *Fusarium* Are Nonorthologous," *Mol. Phylogenetics Evol.*, 7:103-116, 1997.

O'Donnell et al., "Gene genealogies reveal global phylogeographic structure and reproductive isolation among lineages of Fusarium graminearum, the fungus causing wheat scab," *Proc. Natl. Acad. Sci.* USA, 97:7905-7910, 2000.

O'Donnell et al., "Molecular Phylogenetic, Morphological, and Mycotoxin Data Support Reidentification of the Quorn Mycoprotein Fungus as Fusarium venenatum," *Fungal Genet. Biol.*, 23:57-67, 1998.

Reischer et al., "Quantification of Fusarium graminearum in infected wheat by species specific real-time PCR applying a TaqMan Probe," *J. Microbiol. Methods.*, 59:141-146, 2004.

Yli-Mattila et al., "Phylogenetic relationship of Fusarium langsethiae to Fusarium poae and Fusarium sporotrichioides as inferred by IGS, ITS, beta-tubulin sequences and UP-PCR hybridization analysis," *Int. J. Food Microbiol.*, 95:267-285, 2004.

* cited by examiner

SEQUENCE LISTING

```
<160> NUMBER OF SEQ ID NOS: 9

<210> SEQ ID NO 1
<211> LENGTH: 15
<212> TYPE: DNA
<213> ORGANISM: Artificial
<220> FEATURE:
<223> OTHER INFORMATION: Primer
<220> FEATURE:
<221> NAME/KEY: r
<222> LOCATION: (1)..(1)
<223> OTHER INFORMATION: r is R1 in the specification; R1 is at least
      one nucleic acid residue
<220> FEATURE:
<221> NAME/KEY: m
<222> LOCATION: (10)..(10)
<223> OTHER INFORMATION: m is X1 in the specification; X1 is guanine,
      adenine or inosine
<220> FEATURE:
<221> NAME/KEY: s
<222> LOCATION: (12)..(12)
<223> OTHER INFORMATION: s is X2 in the specification; X2 is cytosine,
      adenine or inosine

<400> SEQUENCE: 1

rtttttcgtm gsagt                                                     15


<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2

gcttgtgttt ttcgtggcag t                                              21


<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3

gcttgtgttt ttcgtagcag t                                              21


<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4

gcttgtattt ttcgtggcag t                                              21


<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5

gcttgtgttt ttcgtggaag t                                              21
```

-continued

```
<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6

ggtctcgaca gcaatggtgt t                                                21


<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7

ggtcttgaca gcaatggtgt t                                                21


<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8

acaacggcac ctctgagctc cagc                                             24


<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9

acaacggtac ctctgagctc cagc                                             24
```

METHOD FOR THE DETECTION OF *FUSARIUM GRAMINEARUM*

This application is a national phase application under 35 U.S.C. §371 of International Application No. PCT/EP2005/053394 filed 14 Jul. 2005, which claims priority to Austrian Patent Application No. A 1209/2004 filed 15 July 2004. The entire text of each of the above-referenced disclosures is specifically incorporated herein by reference without disclaimer.

The present invention relates to methods and kits for the detection of *Fusarium graminearum* (*Gibberella zeae*).

*Fusarium graminearum* Schwabe (teleomorph: *Gibberella zeae* (Schw.) Petch) is an important pathogen of cereal crops, causing root rot and seedling diseases (Cook, 1968; Manka et al., 1985), head blight of wheat and barley (Stoyan et al., 2003), and stalk and ear rot of maize (Cook, 1981; Kommedahl and Windels, 1981). *Fusarium* head blight and ear rot reduce grain yield and the harvested grain is often contaminated with mycotoxins such as trichothecenes and zeralenone (Lee et al., 2002). Trichothecene contamination is associated with feed refusal, vomiting, diarrhoea, dermatitis and haemorrhages (Marasas et al., 1984).

Up to date the identification of the pathogen is relying on conventional methods like the interpretation of visual symptoms or the isolation and culturing of the fungus. The drawback of those methods is that detection of the pathogen is only possible in late stages of the infection when it is already too late for any countermeasures and the spread of the disease cannot be controlled anymore. In contrast, molecular diagnostics of plant pathogenic fungi can be highly specific, very sensitive and relatively fast (McCartney et al., 2003).

In the state of the art several methods are disclosed for the detection of *F. Graminearum*. For instance Edwards et al. (2001) describe a PCR-based method for the identification and the quantification of several *Fusarium* species, including *F. Graminearum*, within harvested grain. For the identification as well as for the quantification primers directed to the trichodiene synthese gene (Tri5) were designed and used in a diagnostic and in a quantitative PCR. The method disclosed in this article allows to distinguish Tri5 harbouring *Fusarium* species from species lacking of Tri5. Therefore an accurate distinction of *Fusarium* species is not possible, because the Tri5 gene is widely spread among *Fusarium* species and is not a characteristic feature of a single species.

WO 99/07884 A1 as well as WO 03/027635 A2 disclose methods for the detection of different fungal pathogenes, including *Fusarium* species, by using a PCR-based technique. The primers employed in these methods are derived from Internal Transcribed Spacer (ITS) DNA sequences of the nuclear ribosomal RNA gene (rDNA) or from the mitochondrial Small Subunit Ribosomal DNA sequences.

Other genes suitable for the characterisation of fungal pathogens comprise the β-tubulin gene. This gene is highly conserved as compared to functional genes and thus allows the development of primers and probes that can reach all members of a group of phylogenetically related organisms at any level (Atkins and Clark, 2004; McCartney et al., 2003). On the other hand the sequence of the β-tubulin genes of *Fusarium* sp. is variable enough to allow distinction between fungi on the species level, which was a requirement for the species-specific detection of *Fusarium graminearum*. As mentioned above another gene target commonly used in this type of assay, are the genes of the ribosomal RNA (rRNA genes) and their intervening Internal Transcribed Spacer regions (ITS), which is too highly conserved in *Fusarium* sp. and does not allow a differentiation on this low level of phylogenetic affiliation (O'Donnell and Cigelnik, 1997). In addition, both mentioned "phylogenetic" genes are well investigated and a large amount of sequence information from fungal isolates and environmental samples is available. That facilitates the development of PCR primers and hybridisation probes and allows a better estimation of the selectivity of the developed tools. The use of the β-tubulin gene for phylogenetic studies and diagnostic applications is a well established practice (Fraaije et al., 1998; O'Donnell et al., 1998; O'Donnell et al., 2000; Yli-Mattila et al., 2004).

U.S. Pat. No. 5,707,802 discloses a PCR method for the detection of pathogenic fungus strains by employing primers specific for a hyper variable region of 28S rDNA or rRNA.

In the international patent application WO 2004/029216 a method for detecting the presence of invasive pathogenic molds in a biological sample by detecting a 5.8S ribosomal RNA fragment of the respective mold via PCR is disclosed.

DE 196 15 934 relates to a method for detecting *Fusarium graminearum* in a sample wherein said detection occurs by the determination of the enzymatic activity of galactose oxidase, binding of antibodies to said oxidase or by using primers specific for the nucleotide sequence of galactose oxidase in a PCR reaction.

Similarly, Knoll et al. (Lett Appl Microbiol (2002) 34: 144-148) disclose a PCR based method for the detection of galactose oxidase of *Fusarium graminearum* in a sample.

Hue et al. (J Clin Microbiol (1999) 37:2434-2438) describe the specific detection of *Fusarium* strains in blood or tissue samples by using an rDNA specific PCR.

Jaeger et al. (J Clin Microbiol (2000) 38: 2902-2908) identified members of *Candida, Aspergillus* and *Fusarium* species in a sample by using a nested PCR specific for a 18S rRNA fragment.

In providing suitable methods for specific detection of microorganisms, techniques developed for strain typing are usually not exact enough for unambiguous identification of a single strain. This unambiguous identification requires identification of strain properties which are unique and which are identifiable by reproduceable and robust methods, especially when conducted on diverse sample material from natural sources. It is therefore an object of the present invention to provide suitable means for the specific detection of *Fusarium graminearum* (*Gibberella zeae*) in a sample allowing a clear differentiation from other *Fusarium* species.

Therefore the present invention provides a method for the detection of *Fusarium graminearum* (*Gibberella zeae*) comprising the steps:

providing a sample containing a nucleic acid, contacting said sample with at least one forward primer and at least one reverse primer, wherein the at least one reverse primer hybridises within the β-tubulin nucleic acid sequence of *Fusarium graminearum* (*Gibberella zeae*) and comprises the nucleic acid sequence 5'-$R_1$TTTTTCGT$X_1$G$X_2$AGT-3' (SEQ ID NO 1), wherein $R_1$ comprises at least one nucleic acid of the β-tubulin nucleic acid sequence located upstream of the hybridisation site of the nucleic acid sequence SEQ ID NO 1 and subsequent to the nucleic acid sequence SEQ ID NO 1, $X_1$ is guanine, adenine or inosine, $X_2$ is cytosine, adenine or inosine, and wherein the at least one forward primer hybridises upstream of the hybridisation site of a nucleic acid sequence complementary to the at least one reverse primer, subjecting the sample contacted with the at least one forward primer and the at least one reverse primer to a nucleic acid amplification technique, and optionally determining the presence of *Fusarium graminearum* (*Gibberella zeae*) in a sample by detecting a nucleic acid amplification product.

"Providing a sample containing a nucleic acid" refers to methods known in the state of the art, which can be employed to isolate a sample containing a nucleic acid. However, nucleic acids can be further isolated from a sample containing nucleic acids, for instance according to methods disclosed in Sambrook, J., and Russell, D. W. (2001) Molecular Cloning, Cold Spring Harbor Laboratory Press, Cold Spring Harbor, N.Y. For certain nucleic acid amplification techniques (e.g. in situ PCR) the isolation of a nucleic acid from a sample is not necessary.

According to the present invention the terms "nucleic acid" and "β-tubulin nucleic acid sequence" refer to DNA as well as to RNA and mRNA.

The term "sample" includes all type of samples, which may be infected by fungi, especially by *F. graminearum* (*G. zeae*). Therefore a sample according to the present invention comprises e.g. cereals and food and food products derived from cereals, soil, garden soil products, animal feed, infected plant material, compost, fungal spores from air, rain and hail.

"Hybridising" is the ability of primers consisting of nucleic acids to bind specifically to a nucleic acid sequence under stringent conditions and under conditions applied in the course of a polymerase chain reaction. Stringent conditions are sequence-dependent and will be different in different circumstances. Longer sequences hybridise specifically at higher temperatures. An extensive guide to the hybridisation of nucleic acids is found in Tijssen, Techniques in Biochemistry and Molecular Biology—Hybridisation with Nucleic Probes, "Overview of principles of hybridisation and the strategy of nucleic acid assays" (1993). Generally, stringent conditions are selected to be about 5 to 10° C. lower than the thermal melting point (Tm) for the specific sequence at a defined ionic strength and pH. The Tm is the temperature (under defined ionic strength, pH, and nucleic acid concentration) at which 50% of the probes complementary to the target hybridise to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides).

The term "at least one" clarifies that according to the present invention one or more forward or reverse primers can be employed in a single or in a multiple series of polymerase chain reactions. Some polymerase chain reaction techniques, e.g. nested PCR, TaqMan®-PCR, employ more than one forward and/or more than one reverse primers.

The β-tubulin nucleic acid sequences are publicly available from databases like the NCBI (available on the World Wide Web at ncbi.nlm.nih.gov/entrez) or the EMBL database (available on the World Wide Web at ch.embnet.org/software/bBLAST.html).

A primer comprising the sequence 5'-$R_1$TTTTCGT$X_2$G$X_3$AGT-3' (SEQ ID NO 1) can be used as reverse primer in combination with an appropriate forward primer in a polymerase chain reaction in order to obtain a specific fragment. If such a fragment is obtained, *F. graminearum* (*G. zeae*) is present in the sample analyzed. This specificity on the species level is achieved by utilising a single diagnostic base (the thymine residue at the 3'-end) that is unique for the β-tubulin gene of *F. graminearum* and is not found in other *Fusarium* species at this position in the gene. This is the only position in the β-tubulin gene's chain 1 where such an exclusive distinction is possible. The reverse primer selectively binds to this diagnostic base. Positioning the primers at any different site would lead to loss of selectivity.

According to a preferred embodiment the at least one reverse primer and/or the at least one forward primer comprise(s) 14 to 50, preferably 16 to 45, more preferably 18 to 40, more preferably 19 to 35, especially 20 to 30, nucleic acid residues. The length of the at least one primer, which can influence its binding specificity to the nucleic acid template, can be varied depending on the nucleic acid amplification technique and reaction conditions.

According to another preferred embodiment the at least one reverse primer is selected from the group consisting of 5'-GCTTGTGTTTTTCGTGGCAGT-3' (SEQ ID NO 2), 5'-GCTTGTGTTTTTCGTAGCAGT-3' (SEQ ID NO 3), 5'-GCTTGTATTTTTCGTGGCAGT-3' (SEQ ID NO 4) and 5'-GCTTGTGTTTTTCGTGGAAGT-3' (SEQ ID NO 5). These reverse primers can alternatively be used, without loosing the specificity in detecting *F. graminearum* (*G. Zeae*).

The nucleic acid amplification technique is preferably a polymerase chain reaction technique.

According to a preferred embodiment the polymerase chain reaction technique is selected from the group consisting of realtime PCR, preferably TaqMan® PCR, quantitative PCR, nested PCR, assymetric PCR, multiplex PCR, inverse PCR, rapid PCR and combinations thereof. According to the present invention every polymerase chain reaction technique known in the state of the art can be used to detect *F. graminearum* (*G. Zeae*).

According to a preferred embodiment the at least one forward primer hybridises within the β-tubulin cluster of *Fusarium graminearum* (*Gibberella zeae*). Also forward primers hybridising not within the β-tubulin cluster can be used for detecting *F. graminearum* (*G. Zeae*) in a sample, if these primers are located upstream of the β-tubulin gene where the at least one reverse primer is derived from.

Preferably the at least one forward primer is derived from *F. graminearum* (*G. zeae*) and hybridises in a distance of at least 25, at least 50, at least 75, at least 100, at least 150, at least 200, at least 300, at least 400, at least 500 or at least 1000 nucleic acid residues to the at least one reverse primer. Forward primers can easily be designed on the basis of the DNA template.

According to a preferred embodiment the nucleic acid fragment obtained by the nucleic acid amplification according to the present invention comprises at least 50, at least 80, at least 110, at least 150, at least 200, at least 300, at least 400, at least 500 or at least 1000 nucleic acids.

According to another preferred embodiment the at least one forward primer comprises the sequence 5'-GGTCTCGACAGCAATGGTGTT-3' (SEQ ID NO 6) or 5'-GGTCTTGACAGCAATGGTGTT-3' (SEQ ID NO 7). Both primers hybridise within the β-tubulin cluster of *F. graminearum* (*G. zeae*) and are located upstream of the at least one reverse primer.

Preferably the polymerase chain reaction is performed with at least one oligonucleotide probe hybridising in between of the at least one forward primer and the at least one reverse primer within the β-tubulin cluster of *Fusarium graminearum* (*Gibberella zeae*).

According to a another preferred embodiment the at least one oligonucleotide probe is tagged with a dye, preferably a fluorescent dye, and optionally with a quencher. An additional oligonucleotide, which hybridises between the at least one forward and the at least reverse primer within the β-tubulin cluster and is tagged with a dye and a quencher (e.g.

FAM/TAMRA), is added to the PCR reaction mixture in order to visualise the nucleic acid fragment already during the synthesis in a thermocycler (quantitative PCR). Furthermore the addition of another oligonucleotide enhances the specificity and yield of a PCR.

Preferably the at least one oligonucleotide probe comprises the sequence 5'-ACAACGGCACCTCTGAGCTCCAGC-3' (SEQ ID NO 8) or 5'-ACAACGGTACCTCTGAGCTCCAGC-3' (SEQ ID NO 9).

According to a preferred embodiment of the present invention the amplified nucleic acid fragment is additionally tagged for visualisation by a technique selected from the group consisting of DNA-tagging by random-priming, DNA-tagging by nick-translation, DNA-tagging by polymerase chain reaction, oligonucleotide tailing, hybridisation, tagging by kinase activity, fill-in reaction applying Klenov fragment, photobiotinylation and combinations thereof. Due to a tagging of the PCR product this product can easily be visualised by an additional further step involving e.g. gel electrophoresis.

Preferably the amplified nucleic acid fragment is visualised by gel electrophoresis, Southern-blot, photometry, chromatography, colorimetry, fluorography, chemoluminescence, autoradiography, detection by specific antibody and combinations thereof.

According to another aspect, the present invention relates to a kit for the detection of *Fusarium graminearum* (*Gibberella zeae*) comprising at least one forward primer and at least one reverse primer, wherein the at least one reverse primer hybridises within the β-tubulin cluster of *Fusarium graminearum* (*Gibberella zeae*) and comprises the nucleic acid sequence 5'-$R_1$TTTTCGT$X_1$G$X_2$AGT-3' (SEQ ID NO 1), wherein $R_1$ comprises at least one nucleic acid residue of the β-tubulin nucleic acid sequence located upstream of the hybridisation site of the nucleic acid sequence SEQ ID NO 1 and subsequent to the nucleic acid sequence SEQ ID NO 1, $X_1$ is guanine, adenine or inosine, $X_2$ is cytosine, adenine or inosine, and wherein the at least one forward primer hybridises upstream of the hybridisation site of a nucleic acid sequence complementary to the at least one reverse primer.

According to another aspect, the present invention relates to a use of at least one forward primer and at least one reverse primer, wherein the at least one reverse primer hybridises within the β-tubulin cluster of *Fusarium graminearum* (*Gibberella zeae*) and comprises the nucleic acid sequence 5'-$R_1$TTTTCGT$X_1$G$X_2$AGT-3' (SEQ ID NO 1), wherein $R_1$ comprises at least one nucleic acid residue of the β-tubulin nucleic acid sequence located upstream of the hybridisation site of the nucleic acid sequence SEQ ID NO 1 and subsequent to the nucleic acid sequence SEQ ID NO 1, $X_1$ is guanine, adenine or inosine, $X_2$ is cytosine, adenine or inosine, and wherein the at least one forward primer hybridises upstream of the hybridisation site of a nucleic acid sequence complementary to the at least one reverse primer, for the detection of *Fusarium graminearum* (*Gibberella zeae*).

The developed primers and probes may also serve as basis for other detection methods such as SYBR green real-time PCR (using only the diagnostic primer pair), other probe dependent real-time PCR methods e.g. Molecular Beacon or Scorpion primer-probes. In addition it shall be noted that the applied probe sequence can be utilised for the design of a FISH (Fluorescent InSitu Hybridisation) probe used to monitor the propagation of the plant pathogen in the respective plant tissue.

The chosen diagnostic fragment bears the potential for designing primer/probe combinations for a species-specific detection of additional *Fusarium* species, especially other head blight agents.

The present invention is further illustrated by the following example and figures, yet without being restricted thereto.

EXAMPLE

Figure 1:
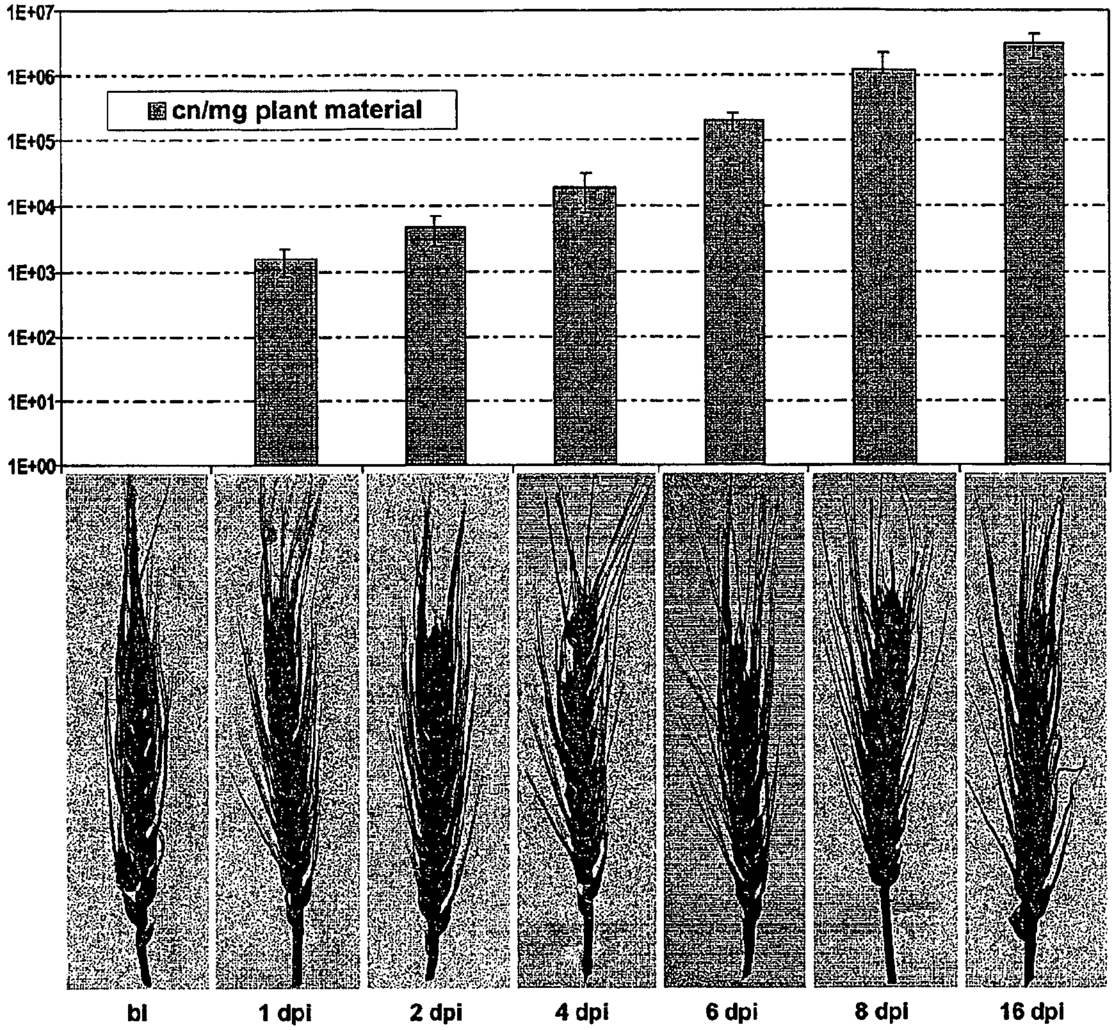
FIG. 1 shows β-tubulin gene copy numbers per mg (cn/mg) of plant material (wet weight) detected with the real-time PCR assay in samples taken from the inoculation experiment before infection (bi) and during all stages of infection 1, 2, 4, 6, 8 and 16 days post infection (dpi). Columns represent the median value of 27 separate measurements for each day, error bars indicate the maximum and minimum values, respectively. Below, pictures of the respective wheat spikes are shown.
Figure 2:
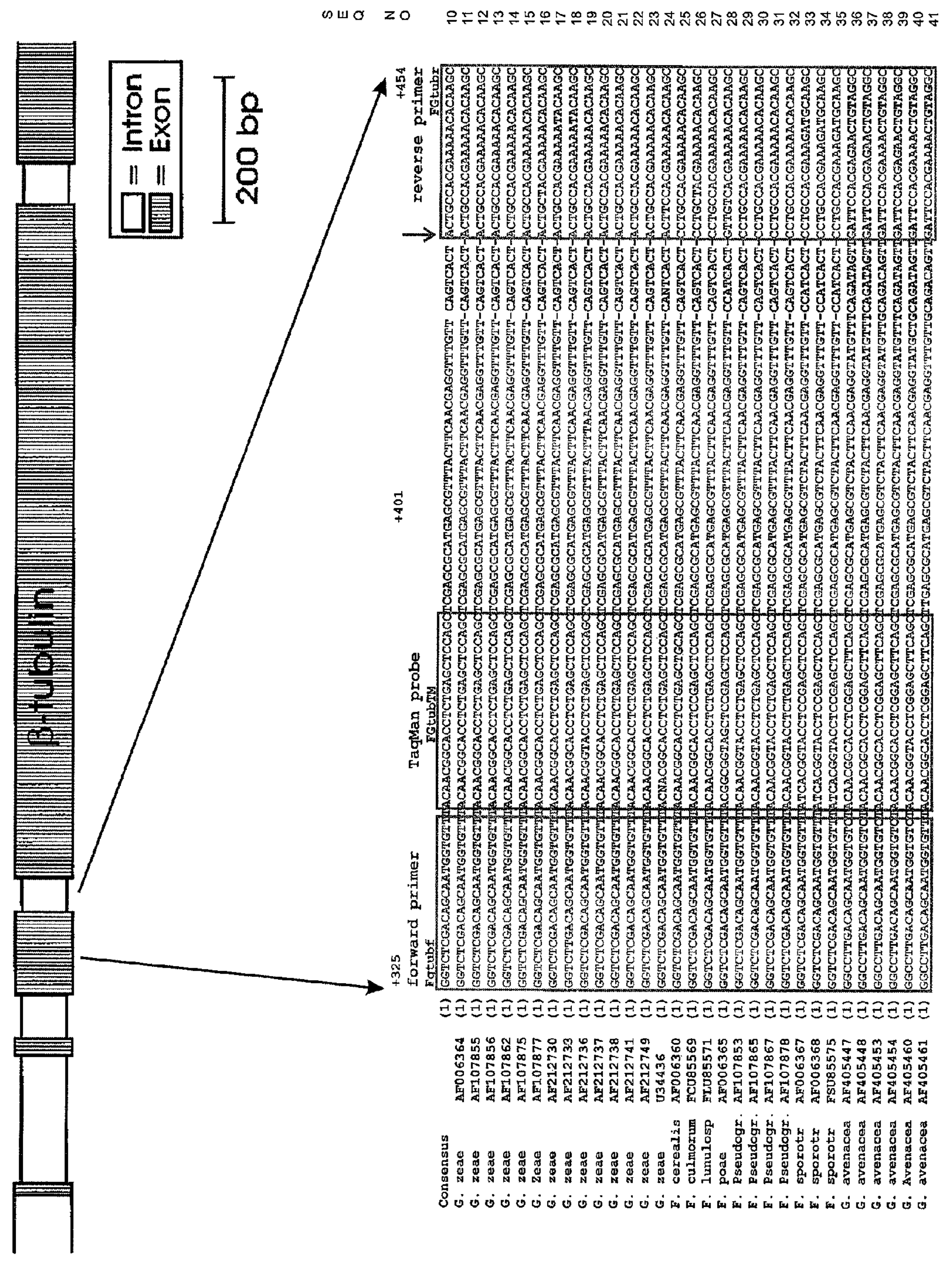
FIG. 2 is a schematic drawing of the diagnostic fragment of the β-tubulin gene. Various *Fusarium* β-tubulin gene sequences (SEQ ID NOs: 10-41) (taken from publicly available databases; database accession numbers are cited next to the organism name) were aligned (using the Vector NTI software package) to identify a species specific primer/probe combination highlighted in boxes. The species specific reverse primer FGtubr is positioned within the third intron of the β-tubulin gene, the species specific base is situated at the 3' end of the primer (indicated with an arrow). The positioning of the diagnostic fragment is given in the figure and is related to the *Fusarium graminearum* β-tubulin sequence.

Species-Specific Identification and Absolute Quantification of *F. graminearum* in Planta by a Real-Time PCR Assay Using a Taqman® Hybridisation Probe The method according to the present invention was tested on plant material from wheat artificially infected in open field experiment.

Materials and Methods

DNA of pure cultures from the strain collections of the Institute of Chemical Engineering and the IFA Tulln (see Table 1) was extracted following the method previously described by Arisan-Atac et al., 1995. DNA from wheat spikes of defined weight was obtained by grinding of whole spikes in liquid nitrogen, taking an aliquot of 50 μg from the homogenate and subsequent DNA extraction as described by Arisan-Atac et al., 1995 with the following modifications: a bead-beating step using a Fast-Prep FP 120 (Thermo Savant, Holbrook, N.Y.) at an intensity setting of 6 for 30 sec was introduced after addition of CTAB buffer, followed by a phenol-chloroform-isoamyl alcohol (25:24:1) extraction (Griffiths et al., 2000). The purified DNA was resuspended in 50 μl of sterile distilled water and stored at −80° C. DNA extraction from wheat spikes was done from 3 different aliquots of each spike to compensate for variations in extraction efficiency.

In addition to the beta-tubulin sequences of 9 Austrian *F. graminearum* isolates (Table 1), a total number of 191 sequences of *F. graminearum* and fungal species either closely related on the beta-tubulin sequence level (O'Donnell et al., 1998) or also associated with head blight in wheat (Edwards et al., 2001) (*F. graminearum [*47], *F. poae [*75], *F. sporotrichoides [*36], *F. pseudograminearum [*18], *F. cerealis [*6], *F. culmorum [*2], *F. lunulosporum [*1] and *G. avenacea [*6]) were extracted from the NCBI database and aligned using the Vector NTI software package (InforMax Inc., Frederick, Md.). Primers were designed from the derived consensus sequence with the Primer Express® software (Applied Biosystems, Foster City, Calif.). The primers FGtubf (5'-GGTCTCGACAGCAATGGTGTT-3') (SEQ ID NO 6) and FGtubr (5'-GCTTGTGTTTTTCGTGGCAGT-3') (SEQ ID NO 2) specifically amplified a 111 by fragment of the beta-tubulin gene of *F. graminearum* which is quantified by the TaqMan® probe FGtubTM (FAM-5'ACAACGGCACCTCT-GAGCTCCAGC3'-TAMRA) (SEQ ID NO 8). The primers and probe were analysed for specificity in-silico by blast analysis using the NCBI Blast feature (available on the World Wide Web at ncbi.nlm.nih.gov/BLAST).

A total of six 10-fold dilution steps of plasmid standard (10-$10^6$ gene copies) were run in triplicate on every wellplate as well as a no-template control (water instead of sample) and a no-amplification control (containing plasmid standard and 0.01% SDS). PCR efficiency was calculated from threshold cycles of these standard dilution steps. As a positive control the DNA extracts from all used isolates were also tested with the beta-tubulin PCR assay targeting all *Fusarium* species described in Yli-Mattila et al., 2004. GenBank accession numbers for beta-tubulin sequences obtained from 16 Austrian *Fusarium* isolates used in this study are included in Table 1.

TABLE 1

| Isolate | Origin[a] | Host | GenBank accession number | Detected in general β-tubulin assay | Detected in TaqMan assay |
|---|---|---|---|---|---|
| *F. graminearum* IFA 66 | IFA | durum wheat kernel | AY635186 | + | + |
| *F. graminearum* IFA 75 | IFA | maize kernel | AY629348 | + | + |
| *F. graminearum* IFA 77.1 | IFA | durum wheat kernel | AY629350 | + | + |
| *F. graminearum* IFA 103 | IFA | maize kernel | AY629342 | + | + |
| *F. graminearum* IFA 110 | IFA | maize kernel | AY629343 | + | + |
| *F. graminearum* IFA 126 | IFA | winter wheat kernel | AY629344 | + | + |
| *F. graminearum* IFA 141 | IFA | soil | AY629345 | + | + |
| *F. graminearum* IFA 165 | IFA | winter wheat kernel | AY629346 | + | + |
| *F. graminearum* IFA 191 | IFA | maize kernel | AY629347 | + | + |
| F. sp. IFA 76 | IFA | phragmites | AY629349 | + | − |
| *F. cerealis* MA 1888 | ICE | maize kernel | AY635180 | + | − |
| *F. cerealis* MA 1891 | ICE | maize kernel | AY635181 | + | − |
| *F. culmorum* MA 1900 | ICE | maize kernel | AY635182 | + | − |
| *F. culmorum* MA 1901 | ICE | maize kernel | AY635183 | + | − |
| *F. culmorum* MA 1902 | ICE | maize kernel | AY635184 | + | − |
| *F. culmorum* MA 1903 | ICE | maize kernel | AY635185 | + | − |
| *F. poae* IBT 9988 | ICE | oat | AF404192 | + | − |
| *F. poae* IBT 9991 | ICE | oat | AF404208 | + | − |
| *F. sporotrichoides* IBT 40004 | ICE | wheat glume | AF404149 | + | − |

[a]ICE, *Fusarium* strain collection Institute of Chemical Engineering, Vienna, Austria; IFA strain collection of IFA, Tulln, Austria.

For the generation of a plasmid standard a 570 bp fragment of the beta-tubulin gene of *F. graminearum* isolate IFA 66 encompassing the target region of the real-time assay was cloned into a pGEM-T Vector (Promega, Madison, Wis.). After transformation of *Escherichia coli* JM 109 with the plasmid and purification of the plasmid DNA with the Plasmid Midi Kit (Qiagen, Hilden, Germany), the concentration of the plasmid standard solution was measured photometrically and the standard was diluted in 10 fold steps in a 10 ng/μl poly [d(I-C)] solution as unspecific DNA background (Roche Diagnostics, Mannheim, Germany).

PCR was monitored on an iCycler iQ Real-Time Detection System (Biorad, Hercules, Calif.). Reaction mixtures (25 μl total volume) contained 2.5 μl of template DNA dilution, 7.5 pmol of FGtubf, 7.5 pmol of FGtubr, 6.25 pmol of FGtubTM, 12.5 μl of iQ Supermix (Biorad) and 10 μl of sterile bi-distilled water. The PCR programme was the following: 95° C. for 3 min 30 sec (denaturation, activation of polymerase, measuring of well factors), 40 cycles of 95° C. for 15 s, 67° C. for 15 s and 72° C. for 20 s. All reactions were performed in triplicates and in at least three 10-fold dilution steps of template DNA. The number of cycles in the PCR was set to 40, as the 40th cycle represents the extrapolated threshold cycle for a reaction with a theoretical single copy of the template DNA.

For artificial inoculation of wheat in the field experiment the IFA 191 isolate was used (*F. graminearum* isolated from a *Triticum durum* kernel in 1990 in Austria). It was stored (at 2-4° C.) in soil cultures for stable long-term storage (Smith and Onions, 1994). Inoculum was prepared with the bubble breeding method (Mesterházy, 1978). A modified Czapek-Dox medium (containing/l of bi-distilled water in g: glucose, 20; $KH_2PO_4$, 0.5; $NaNO_3$, 2; $MgSO_4.7H_2O$, 0.5; yeast extract, 1 and 1 ml of a 1% $FeSO_4$ solution (w/w)) supplemented with 0.1 g streptomycin sulphate/l and 0.01 g neomycin/l after autoclaving was used for inoculum production. After 1 week the mycelium suspension was ready and 300 ml of the suspension was diluted in 1 l of bi-distilled water for inoculation.

The wheat line E2-23-T was grown in 2 $m^2$ plots at the IFA experimental field. This wheat line is a doubled haploid line originating from a cross between CM82036 and Remus and was produced with the maize-wheat pollination system. It is a very susceptible line and does not have a quantitative trait locus (QTL) for *Fusarium* head blight resistance on chromosome 5A and 3B (Buerstmayr et al., 2002; Buerstmayr et al., 2003).

The wheat line was inoculated at 50% anthesis by spraying 100 ml/$m^2$ of the inoculum suspension described above. To promote infection an automated mist irrigation system was used to apply moisture. Water was applied in 2 pulses of 10 s each at 15 min intervals during 17 hours after inoculation. Before inoculation 10 flowering spikes were cut and removed from the plot. On day 1, 2, 4, 6, 8 and 16 after inoculation the sampling procedure was repeated. All spikes were immediately stored at −80° C. after sampling for further investigations.

RESULTS

The primers, probe and PCR protocol were evaluated by amplifying DNA from pure culture isolates of *F. graminearum* as well as the developed plasmid standard. Specificity was assessed by amplification of DNAs from various isolates which are either closely related to *F. graminearum* and/or also causing head blight in wheat. The β-tubulin gene of all non *F. graminearum* isolates failed to be amplified in the reaction while DNA from all isolates yielded products in the general *Fusarium* PCR assay (Table 1). All PCR products were of the expected size when examined by agarose gel electrophoresis.

All *F. graminearum* isolates tested could be detected with the developed method. Interestingly one additional *Fusarium* isolate originally included in the group of *F. graminearum* isolates, was presumptively identified by sequence comparison to actually be closer related to *F. flocciferum* (O'Donnell et al., 1998). Despite only one mismatch in nucleotide sequence in the binding area of the TaqMan® probe this isolate was not detected by our PCR approach. The amplification of the standard dilution series yielded linear and reliable results ($R^2>0.997$) in the range from 10 to $10^6$ copies of the beta-tubulin gene per PCR reaction (range of quantitation). The qualitative detection limit for the beta-tubulin gene was as low as 5 gene copies.

In the next step the efficiency of the amplification was investigated using plasmid standard as well as known amounts of *F. graminearum* sample isolate DNA as template in the presence of unspecific DNA, such as the DNA from isolates closely related to *F. graminearum* (Table 1) and DNA extracted from uninfected wheat spikes. No change in threshold cycle values could be observed under these conditions as compared to amplification without a DNA background. In addition the overall efficiency of the PCR amplification was very high regardless of template origin or unspecific DNA background (95-98.8%).

The developed method was applied on the total DNA extracted from spikes of infected wheat plants in all states of infection. The β-tubulin gene could not be detected in samples from uninfected wheat. However, detection was possible in all samples taken after inoculation with *F. graminearum* isolate IFA 191. There was a distinct gradual increase in gene copies measured, corresponding to the fungal growth during the infection of the wheat spike (FIG. 1). Detection was possible from the first day post inoculation, while first symptoms of the infection (water soaked spots) appeared 7 to 10 days after inoculation (see FIG. 1). Data of all aliquots, dilution steps and replicates are included in FIG. 1.

The method according to the present invention allows a fast, species-specific identification and quantitation of plant-infections by *F. graminearum* at very early stages where classical microbiological and toxin analysis methods fail to detect the pathogen (McCartney et al., 2003). It can be applied on DNA extracted directly from presumptively infected plant material and is not affected by an unspecific background of either plant or fungal DNA, even from other pathogens causing head blight. It allows a reliable estimation of the fungal genomes and can detect as few as 5 gene copies. The assay is cheaper and less time consuming than microbiological identification methods. The range of reliable quantification was higher than in studies published previously where the linearity was only achieved over 4 to 5 orders of magnitude (Cullen et al., 2001; Filion et al., 2003; Winton et al., 2002).

Combined with the analysis of genes contributing to the trichothecene production the presented method will be an invaluable tool for the study of *F. graminearum* infection processes. The sensitivity of the method would even allow the quantitation of fungal growth in different plant tissues during the progress of infection (Stoyan et al., 2003). Due to its simplicity it could also be used in routine analysis and the monitoring of *F. graminearum* epidemics or the monitoring of pest control measures.

REFERENCES

Arisan-Atac, I., Heidenreich, E., Kubicek, C. P., 1995. FEMS Microbiol. Lett. 126, 249-255.

Buerstmayr, H., Lemmens, M., Hartl, L., Doldi, L., Steiner, B., Stierschneider, M., Ruckenbauer, P., 2002. Theor. Appl. Genet. 104, 84-91.

Buerstmayr, H., et al., 2003. Theor. Appl. Genet. 107, 503-8.

Cook, R. J., 1968. Phytopathology 78, 1673-1677.

Cook, R. J., 1981. In: Nelson, P. E., Toussoun, T. A. (Eds.), *Fusarium* diseases, biology and taxonomy, The Pennsylvania State University Press, University Park, pp. 39-52.

Cullen, D. W., Lees, A. K., Toth, I. K., Duncan, J. K., 2001. Eur. J. Plant Pathol. 107, 387-398.

Edwards, S. G., Pirgozliev, S. R., Hare, M. C., Jenkinson, P., 2001. Appl Environ Microbiol 67, 1575-80.

Filion, M., St-Arnaud, M., Jabaji-Hare, S. H., 2003. J. Microbiol. Methods 53, 67-76.

Griffiths, R. I., Whiteley, A. S., O'Donnell, A. G., Bailey, M. J., 2000. Appl. Environ. Microbiol. 66, 5488-5491.

Kommedahl, T., Windels, C. E., 1981. In: Nelson, P. E., Toussoun, T. A. (Eds.), *Fusarium* diseases, biology and taxonomy, The Pennsylvania State University Press, University Park, pp. 94-103.

Lee, T., Han, Y. K., Kim, K. H., Yun, S. H., Lee, Y. W., 2002. Appl. Environ. Microbiol. 68, 2148-54.

Manka, M., Visconti, A., Chelkoski, J., Bottalico, A., 1985. Phytopathol. Z. 113, 24-29.

Marasas, W. F. O., Nelson, P. E., Toussoun, T. A., 1984. Toxigenic *Fusarium* species: identity and mycotoxicology. The Pennsylvania State University Press, University Park McCartney, H. A., Foster, S. J., Fraaije, B. A., Ward, E., 2003. Pest. Manag. Sci. 59, 129-142.

Mesterházy, A., 1978. J. Phytopathol. 93, 12-25.

O'Donnell, K., Cigelnik, E., Casper, H. H., 1998. Genet. Biol. 23, 57-67.

Schnerr, H., Vogel, R. F., Niessen, L., 2002. Lett. Appl. Microbiol. 35, 121-5.

Smith, D., Onions, A. H. S., 1994. in: IMI Technical Handbooks, Vol. 2, pp. 122 (Institute, I. M., Ed.) Cab International, Wallingford, UK Stoyan, R. P., Edwards, S. G., Hare, M. C., Jenkinson, P., 2003. Plant Pathol. 44, 207-238.

Winton, L. M., Stone, J. K., Watrud, L. S., Hansen, E. M., 2002. Phytopathol. 92, 112-116.

Yli-Mattila, T., Mach, R. L., Alekhina, I. A., Bulat, S. A., Kullnig-Gradinger, C. M., Kubicek, C. P., Klemsdal, S. S., 2004. Int. J. Food Microbiol., In Press.

The invention claimed is:

1. A method for the specific detection of *Fusarium graminearum* (*Gibberella zeae*) comprising:

providing a sample containing a nucleic acid;

contacting said sample with at least one forward primer and at least one reverse primer, wherein the at least one reverse primer hybridizes within the β-tubulin nucleic acid sequence of *Fusarium graminearum* (*Gibberella zeae*) and comprises the nucleic acid sequence 5'-R1TTTTCGTX1GX2AGT-3' (SEQ ID NO: 1), wherein R1 comprises at least one nucleic acid residue of the β-tubulin nucleic acid sequence located upstream of the hybridization site of the nucleic acid sequence SEQ ID NO: 1 and subsequent to the nucleic acid sequence SEQ ID NO: 1, X1 is guanine, adenine or inosine, X2 is cytosine, adenine or inosine, and wherein the at least one forward primer hybridizes upstream of the hybridization site of a nucleic acid sequence complementary to the at least one reverse primer; and subjecting the sample contacted with the at least one forward primer and the at least one reverse primer to a nucleic acid amplification technique.

2. The method of claim 1, further comprising determining the presence of *Fusarium graminearum* (*Gibberella zeae*) in the sample by detecting a nucleic acid amplification product.

3. The method of claim 1, wherein the at least one reverse primer and/or the at least one forward primer comprise(s) 14 to 50 nucleic acid residues.

4. The method of claim 3, wherein the at least one reverse primer and/or the at least one forward primer comprise(s) 16 to 45 nucleic acid residues.

5. The method of claim 4, wherein the at least one reverse primer and/or the at least one forward primer comprise(s) 18 to 40 nucleic acid residues.

6. The method of claim 5, wherein the at least one reverse primer and/or the at least one forward primer comprise(s) 20 to 30 nucleic acid residues.

7. The method of claim 1, wherein the at least one reverse primer is 5'-GCTTGTGTTTTTCGTGGCAGT-3' (SEQ ID NO: 2), 5'-GCTTGTGTTTTTCGTAGCAGT-3' (SEQ ID NO: 3), 5'-GCTTGTATTTTTCGTGGCAGT-3' (SEQ ID NO: 4), or 5'-GCTTGTGTTTTTCGTGGAAGT-3' (SEQ ID NO: 5).

8. The method of claim 1, wherein the nucleic acid amplification technique is a polymerase chain reaction technique.

9. The method of claim 8, wherein the polymerase chain reaction technique is real-time PCR, quantitative PCR, nested PCR, assymetric PCR, multiplex PCR, inverse PCR, rapid PCR, or a combination thereof.

10. The method of claim 9, wherein the polymerase chain reaction technique is real-time PCR further defined as TaqMan® PCR.

11. The method of claim 1, wherein the at least one forward primer hybridizes within the β-tubulin cluster of *Fusarium graminearum* (*Gibberella zeae*).

12. The method of claim 1, wherein the at least one forward primer comprises the sequence 5'-GGTCTCGACAG-CAATGGTGTT-3' (SEQ ID NO: 6) or 5'-GGTCTTGACAG-CAATGGTGTT-3' (SEQ ID NO: 7).

13. The method of claim 1, wherein the nucleic acid amplification technique is performed with at least one oligonucleotide probe hybridizing in between the at least one forward primer and the at least one reverse primer within the β-tubulin cluster of *Fusarium graminearum* (*Gibberella zeae*).

14. The method of claim 13, wherein the at least one oligonucleotide probe is tagged with a dye.

15. The method of claim 14, wherein the dye is a fluorescent dye.

16. The method of claim 14, wherein the least one oligonucleotide probe is tagged with a quencher.

17. The method of claim 1, wherein the at least one oligonucleotide probe comprises the sequence 5'-ACAACG-GCACCTCTGAGCTCCAGC-3' (SEQ ID NO: 8) or 5'-ACAACGGTACCTCTGAGCTCCAGC-3' (SEQ ID NO: 9).

18. The method of claim 1, wherein the amplified nucleic acid product is additionally tagged for detection by DNA-tagging by random-priming, DNA-tagging by nick-translation, DNA-tagging by polymerase chain reaction, oligonucleotide tailing, hybridization, tagging by kinase activity, fill-in reaction applying Klenov fragment, photobiotinylation, or a combination thereof.

19. The method of claim 1, wherein the amplified nucleic acid product is detected by gel electrophoresis, Southern-blot, photometry, chromatography, colorimetry, fluorography, chemoluminscence, autoradiography, detection by specific antibody, or a combination thereof.

20. A kit for the specific detection of *Fusarium graminearum* (*Gibberella zeae*) comprising at least one forward primer and at least one reverse primer, wherein the at least one reverse primer hybridizes within the β-tubulin cluster of *Fusarium graminearum* (*Gibberella zeae*) and comprises the nucleic acid sequence 5'-R1TTTTCGTX1GX2AGT-3' (SEQ ID NO: 1), wherein R1 comprises at least one nucleic acid residue of the β-tubulin nucleic acid sequence located upstream of the hybridization site of the nucleic acid sequence SEQ ID NO: 1 and subsequent to the nucleic acid sequence SEQ ID NO: 1, X1 is guanine, adenine or inosine, X2 is cytosine, adenine or inosine, and wherein the at least one forward primer hybridizes upstream of the hybridization site of a nucleic acid sequence complementary to the at least one reverse primer.

21. The kit of claim 20, wherein the at least one reverse primer and/or the at least one forward primer comprise(s) 14 to 50 nucleic acid residues.

22. The kit of claim 21, wherein the at least one reverse primer and/or the at least one forward primer comprise(s) 16 to 45 nucleic acid residues.

23. The kit of claim 22, wherein the at least one reverse primer and/or the at least one forward primer comprise(s) 18 to 40 nucleic acid residues.

24. The kit of claim 23, wherein the at least one reverse primer and/or the at least one forward primer comprise(s) 20 to 30 nucleic acid residues.

25. The kit of claim 20, wherein the at least one reverse primer is 5'-GCTTGTGTTTTTCGTGGCAGT-3' (SEQ ID NO: 2), 5'-GCTTGTGTTTTTCGTAGCAGT-3' (SEQ ID NO: 3), 5'-GCTTGTATTTTTCGTGGCAGT-3' (SEQ ID NO: 4), or 5'-GCTTGTGTTTTTCGTGGAAGT-3' (SEQ ID NO: 5).

26. The kit of claim 20, wherein the at least one forward primer hybridizes within the β-tubulin cluster of *Fusarium graminearum* (*Gibberella zeae*).

27. The kit of claim 20, wherein the at least one forward primer comprises the sequence 5'-GGTCTCGACAG-CAATGGTGTT-3' (SEQ ID NO: 6) or 5'-GGTCTTGACAG-CAATGGTGTT-3' (SEQ ID NO: 7).

28. The kit of claim 20, wherein the kit comprises at least one oligonucleotide probe hybridizing in between the at least one forward primer and the at least one reverse primer within the β-tubulin cluster of *Fusarium graminearum* (*Gibberella zeae*).

29. The kit of claim 28, wherein the at least one oligonucleotide probe is tagged with a dye.

30. The kit of claim 29, wherein the dye is a fluorescent dye.

31. The kit of claim 29, wherein the at least one oligonucleotide probe is tagged with a quencher.

32. The kit of claim 29, wherein the at least one oligonucleotide probe comprises the sequence 5'-ACAACGGCAC-CTCTGAGCTCCAGC-3' (SEQ ID NO: 8) or 5'-ACAACG-GTACCTCTGAGCTCCAGC-3' (SEQ ID NO: 9).

* * * * *